United States Patent
Sung et al.

(10) Patent No.: US 8,692,039 B2
(45) Date of Patent: Apr. 8, 2014

(54) METHOD AND DEVICE FOR SYNTHESIZING RADIOACTIVE METHYL IODIDE TRACER

(75) Inventors: Ki Bang Sung, Daejeon (KR); Ho Yeon Yang, Daejeon (KR); Ji Hoon Lee, Daejeon (KR); Jin Soo Choi, Daejeon (KR); Tae Won Hwang, Daejeon (KR)

(73) Assignee: Korea Hydro & Nuclear Power Co., Ltd., Gyeongsangbuk-do (KR)

( * ) Notice: Subject to any disclaimer, the term of this patent is extended or adjusted under 35 U.S.C. 154(b) by 0 days.

(21) Appl. No.: 13/181,470

(22) Filed: Jul. 12, 2011

(65) Prior Publication Data

US 2012/0209035 A1 Aug. 16, 2012

(30) Foreign Application Priority Data

Feb. 14, 2011 (KR) .................... 10-2011-0012951

(51) Int. Cl.
*C07C 17/20* (2006.01)

(52) U.S. Cl.
USPC ...................................... 570/260

(58) Field of Classification Search
None
See application file for complete search history.

(56) References Cited

FOREIGN PATENT DOCUMENTS

| CN | 1687105 A | 10/2005 |
|---|---|---|
| CN | 1995020 A | 7/2007 |
| WO | WO 01/58434 A2 | 8/2001 |

OTHER PUBLICATIONS

Introduction to Organic Laboratory Techniques A Microscale Approach, Pavia et al. 1990, front matter, and 638-663, 668-687.*
E.R.Swart et al., "The Effect of Solvent on a Simple Ion-Dipole Reaction. Part II. The Rate of the Methyl Iodide-Iodide Ion Exchange in Five Different Solvents", Journal of Chemical Society, 1957, pp. 406-410.
M. Kikuchi et al., "A New Method for the Determination of Fractional Fission Yields: The Reactions of Gaseous Methyl Iodide with Fission-Produced Iodine", Radio Chimica Acta, 1972, pp. 54-58.
M. Maeda et al., "Catalysts in Radiohalogen Labelling-2, Catalytic Effects of Insoluble Phosphonates Bound to Polystyrene and Silica Gel on the Iodine Exchange in a Biphase System", The international Journal of Applied Radiation and Isotopes, Nov. 1979, pp. 713-714, vol. 30, No. 1.
Piyush Kumar et al., "Iodoazomycin arabinoside for low-dose-rate isotope radiotherapy: radiolabeling, stability, long-term whole-body clearance and radiation dosimetry estimates in mice", Nuclear Medicine and Biology, 2005, pp. 647-653, vol. 32.
Steven C. Rumsey et al., "Specificity of Ascorbate Analogs for Ascorbate Transport", The Journal of Biological Chemistry, Aug. 13, 1999, pp. 23215-23222, vol. 274, No. 33.

* cited by examiner

*Primary Examiner* — Clinton Brooks
(74) *Attorney, Agent, or Firm* — Rabin & Berdo, P.C.

(57) ABSTRACT

Disclosed is a method and device for simply and safely preparing, using a direct synthesis process at room temperature, a radioactive methyl iodine ($CH_3{}^{131}I$) tracer for use in evaluating the ability of impregnated activated carbon to adsorb radioactive organic iodine according to ASTM D 3803 (Standard Test Method for Nuclear-Grade Activated Carbon), in which the tracer can be directly synthesized by mixing radioactive sodium iodide ($Na^{131}I$) with methyl iodine ($CH_3I$) at room temperature under reduced pressure, thus shortening excessive synthesis time and decreasing the probability of radiation exposure due to leakage of volatile material during the distillation.

9 Claims, 5 Drawing Sheets

METHOD AND DEVICE FOR SYNTHESIZING RADIOACTIVE METHYL IODIDE TRACER

CROSS-REFERENCE TO RELATED APPLICATION

This application claims priority to Korean Patent Application No. 10-2011-0012951, filed on Feb. 14, 2011, and all the benefits accruing therefrom under 35 U.S.C. §119, the contents of which in its entirety are herein incorporated by reference.

BACKGROUND OF THE INVENTION

1. Technical Field

The present invention relates to a method and device for synthesizing a radioactive methyl iodine ($CH_3^{131}I$) tracer, and more particularly to a method and device for synthesizing a radioactive methyl iodine tracer suitable for use in evaluating the ability of impregnated activated carbon to adsorb radioactive organic iodine according to ASTM D 3803 (Standard Test Method for Nuclear-Grade Activated Carbon).

2. Description of the Related Art

Performance of impregnated activated carbon used in nuclear power plants must be strictly tested. In order to evaluate the ability of impregnated activated carbon to remove radioactive organic iodine, a radioactive methyl iodine ($CH_3^{131}I$) tracer is utilized under high humidity and atmospheric conditions.

Conventionally, radioactive methyl iodine is synthesized using a device of FIG. 1 by subjecting an anhydrous methanol solution and a concentrated sulfuric acid (c-$H_2SO_4$) solution to mixing, stirring and cooling, adding sodium iodide powder (6.0 g when using 5.2 ml of the anhydrous methanol solution and 1.2 ml of the concentrated sulfuric acid solution) with stirring, performing refluxing at 40° C. and heat distillation, thus separating a secondary reaction product, adding a 5% sodium thiosulfate ($Na_2S_2O_3$) aqueous solution to the secondary reaction product thus isolating methyl iodine, separating the sodium thiosulfate solution layer from the secondary reaction product, and performing washing using distilled water, thereby preparing a radioactive methyl iodine solution at a yield of about 40%. Specifically, the total five steps are applied.

Step 1: Synthesis of methyl iodine (10° C., 30 min)

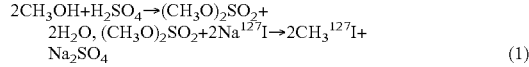

(1)

Step 2: Substitution of methyl iodine and radioactive iodine (40° C., 30 min)

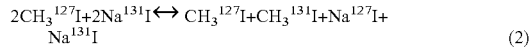

(2)

Step 3: distillation of methyl iodine (60° C., 7 hours)

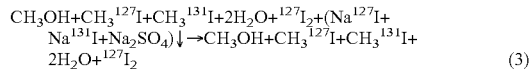

(3)

Step 4: Removal of iodine (30° C., 5 min)

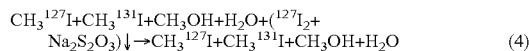

(4)

Step 5: Removal of methyl alcohol and aqua (30° C., 5 min)

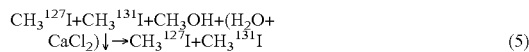

(5)

Briefly, the conventional mechanism for synthesizing a radioactive iodine ($CH_3^{131}I$) tracer includes substituting the ($CH_3O)_2SO_2$ intermediate compound in an aqueous solution state with $^{131}I$ in the steps 1 and 2, thus synthesizing $CH_3^{131}I$.

Because the tracer thus synthesized is present together with a variety of reagents, it is distilled so that volatile $H_2O$, $CH_3OH$, $CH_3^{127}I$, and $CH_3^{131}I$ are distilled from various mixtures, after which only $CH_3^{127, 131}I$ should be purified. As such, only the step 3 including reflux and distillation requires 7 hours or longer, and after completion of the final step 5, about 1 ml of radioactive iodine tracer ($CH_3^{131}I$) may be obtained.

The conventional method of preparing a radioactive methyl iodine tracer is problematic because the radioactive material sodium iodide ($Na^{131}I$) should be handled for a considerable period of time (about 10 hours), and thus workers may be increasingly subjected to external exposure from radioactive sodium iodide due to leakage of the volatile material during the distillation and to internal and external exposure from radioactive methyl iodine ($CH_3^{131}I$).

Furthermore, the conventional method is very complicated because of using radioactive materials such as sodium iodide ($Na^{131}I$), and chemicals such as anhydrous methyl alcohol, concentrated sulfuric acid, sodium thiosulfate, calcium chloride, etc., with the use of a water bath, a low-temperature cooler, a distiller, etc.

SUMMARY OF THE INVENTION

Therefore, the present inventors have intensively and extensively studied minimizing the probability of radiation exposure due to leakage of volatile material during distillation while reducing the synthesis time, and thus have devised a simple device for synthesizing radioactive methyl iodine ($CH_3^{131}I$), thereby completing the present invention.

The present invention has been made keeping in mind the above problems encountered in the related art, and the present invention is intended to provide a method and device for simply and safely synthesizing a radioactive methyl iodine ($CH_3^{131}I$) tracer.

An aspect of the present invention provides a method of preparing a radioactive methyl iodine ($CH_3^{131}I$) tracer using a direct synthesis process comprising mixing radioactive sodium iodide ($Na^{131}I$) with methyl iodine ($CH_3I$) at room temperature under reduced pressure.

Another aspect of the present invention provides a simple device for preparing a radioactive methyl iodine ($CH_3^{131}I$) tracer.

DESCRIPTION OF SPECIFIC EMBODIMENTS

Hereinafter, a detailed description will be given of the present invention.

The present invention pertains to a method of preparing a radioactive methyl iodine ($CH_3^{131}I$) tracer using a direct synthesis process.

Figure 1:
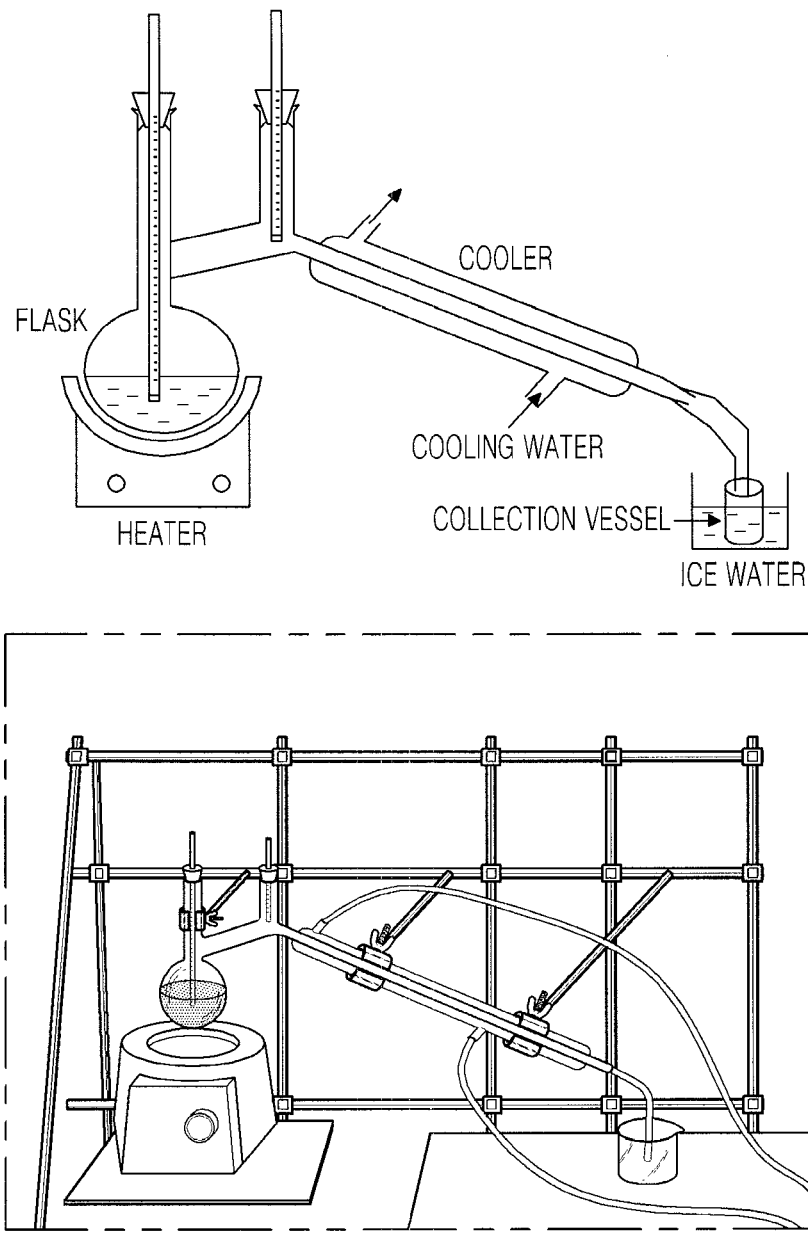
FIG. 1 shows a conventional device for synthesizing a radioactive methyl iodine ($OH_3^{131}I$) tracer.
Figure 2:
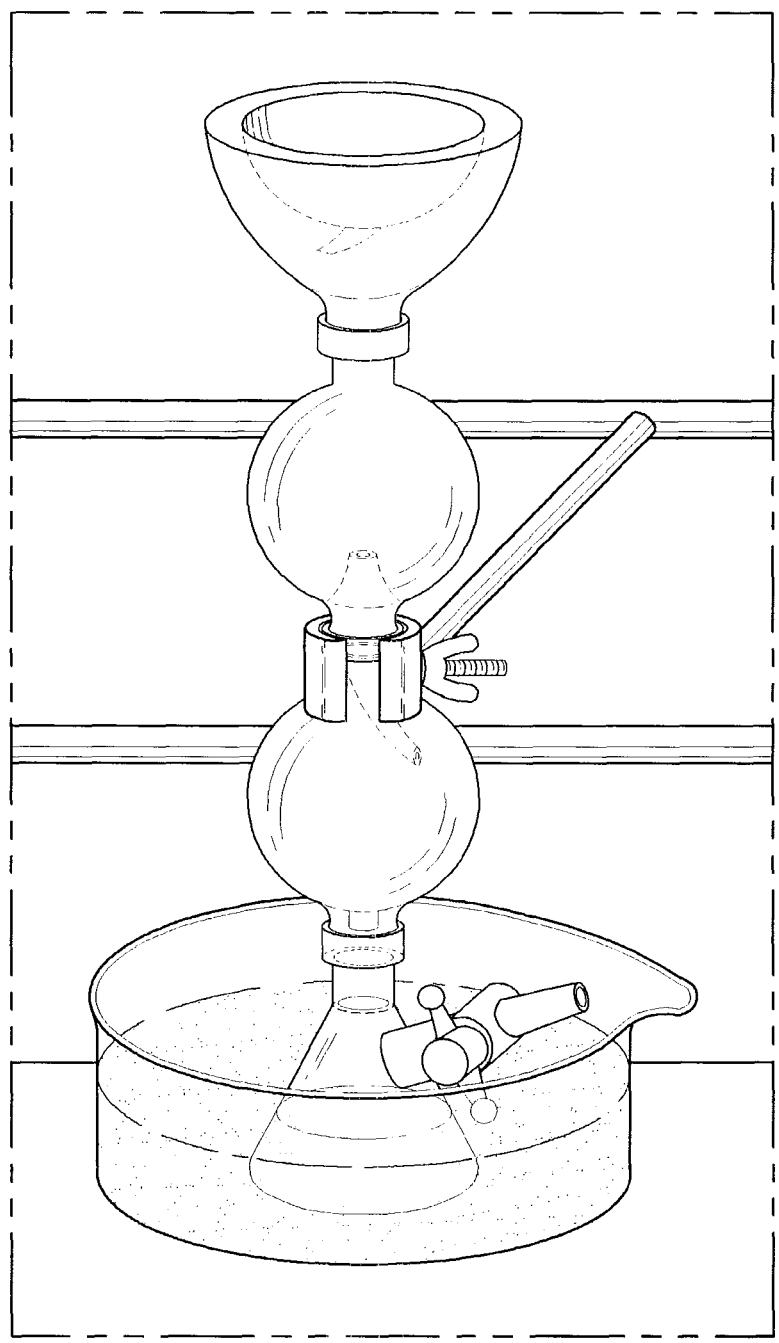
FIG. 2 shows a photograph of a device for synthesizing a radioactive methyl iodine ($CH_3^{131}I$) tracer according to the present invention, which is mounted.

FIG. 2 shows a photograph of a device for synthesizing a radioactive methyl iodine ($CH_3^{131}I$) tracer using a direct synthesis process according to the present invention, which is mounted. Specifically, the synthesis method according to the present invention includes (a) substituting methyl iodine ($CH_3I$) with radioactive iodine ($^{131}I$); and (b) extracting radioactive methyl iodine ($CH_3^{131}I$).

In the method according to the present invention, substitution able to obtain a desired isotope tracer from a water-soluble material (NaI) and a water-insoluble organic compound ($CH_3I$) which do not dissolve in each other does not occur. However, in the case where the water-soluble material (NaI) is radioactive, substitution actively takes place at the boundary of two materials because the radical of iodine is produced by the radiation energy of the material itself.

Using beta ($\beta$) and gamma ($\gamma$) radiation energy ($\beta_{max}$=0.606 MeV, $\gamma$=0.364 MeV) of the radioactive material itself, the isotope usable as the tracer may simply be prepared by substitution, which is represented below.

$$CH_3^{127}I(solv) + Na^{131}I + \beta,\gamma \text{ energy} \leftrightarrow CH_3.(radical) + {}^{127}I.(radical)$$

$$^{127}I. + Na^+ + {}^{131}I^- \leftrightarrow {}^{127}I^- + Na^+ + {}^{131}I.$$

$$^{127}I^- + Na^+ + {}^{131}I. + CH_3. \leftrightarrow CH_3{}^{127}I(solv) + Na^+ + {}^{127}I^-$$

The method of preparing a radioactive methyl iodine ($CH_3^{131}I$) tracer using a direct synthesis process according to the present invention is specified below.

Step 1: Substitution of methyl iodine and radioactive iodine (20° C., 5 min)

$$2CH_3{}^{127}I(\text{org. solv}) + Na^{131}I(\text{aqua}) \leftrightarrow CH_3(^{127}I+^{131}I)(\text{org. solv}) + Na(^{127}I+^{131}I)(\text{aqua}) \quad (6)$$

Step 2: Extraction of radioactive methyl iodine (20° C., 5 min)

$$CH_3(^{127}I+^{131}I) + Na(^{127}I+^{131}I) + H_2O \rightarrow CH_3{}^{127}I + CH_3{}^{131}I \quad (7)$$

Consequently, the method according to the present invention adopts a direct synthesis process including directly mixing radioactive sodium iodide ($Na^{131}I$) and non-radioactive methyl iodine ($CH_3^{127}I$) as the organic solvent which do not mix with each other, at room temperature, thus synthesizing radioactive methyl iodine ($CH_3^{131}I$) and a remainder, which are then separated from each other using distillation. Thereby, it is possible to prepare the radioactive methyl iodine ($CH_3^{131}I$) tracer using the above two steps.

TABLE 1

Conditions and Results of Synthesizing Inventive and Conventional Radioactive Methyl Iodine Tracer

|   | Inventive | Conventional |
|---|---|---|
| RI Tracer | $Na^{131}I$ 3 ml (5 mCi) | $Na^{131}I$ 3 ml (5 mCi) |
| Reagent | RI (Radioactive Isotope) $CH_3{}^{127}I$ (2 ml) | RI (Radioactive Isotope), $CH_3OH$ (4.2 ml) Conc-$H_2SO_4$ (1.2 ml) $Na^{127}I$ (6 g), $Na_2S_2O_3$, $CaCl_2$ Ice, $H_2O$ |
| Synthesis Time | 6 hr | 10 hr |
| Test Time | 10 min | 100 min |
| Product | ($CH_3{}^{127}I + CH_3{}^{131}I$) 3 ml | ($CH_3{}^{127}I + CH_3{}^{131}I$) 1 ml |
| Yield | 50% | 40% |

In addition, the present invention pertains to a simple device that synthesizes the radioactive methyl iodine ($CH_3^{131}I$) tracer.

Figure 3:
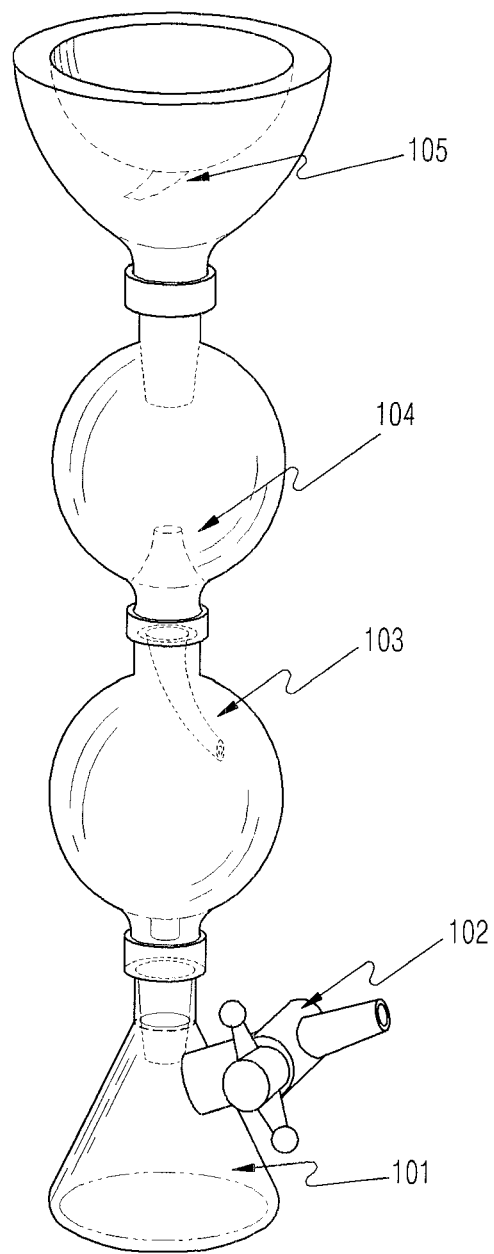
FIG. 3 shows the device for synthesizing radioactive methyl iodine ($CH_3^{131}I$) according to the present invention.
Figure 4:
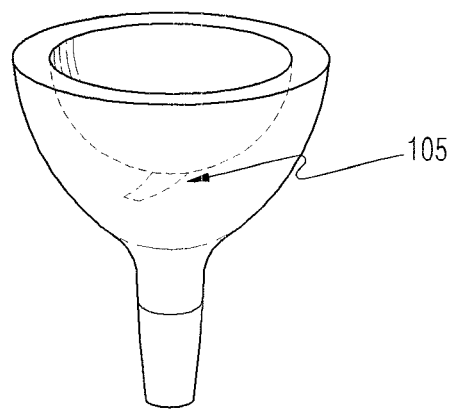
FIG. 4 shows the methyl iodine condenser-collector of the device for synthesizing radioactive methyl iodine ($CH_3^{131}I$) according to the present invention.

FIG. 3 shows the device for synthesizing a radioactive methyl iodine ($CH_3^{131}I$) tracer according to the present invention. The device for synthesizing a radioactive methyl iodine tracer according to the present invention includes a radioactive methyl iodine synthesis flask 101, a pressure reducing valve 102, a methyl iodine-vapor fractionation unit 103, a methyl iodine-vapor condensate separator 104, and a gaseous methyl iodine condenser-methyl iodine condensate collector 105.

The device according to the present invention enables the condensation and recovery of methyl iodine gasified in the device by means of low-temperature distillation using cold water or ice without the use of a power source, and the gaseous methyl iodine condenser-methyl iodine condensate collector 105 includes an uncinate guiding unit for preventing the condensate from dropping straight down.

With reference to FIG. 2, functions and properties of respective parts of the device according to the present invention are specified below.

In the present invention, substitution of methyl iodine and radioactive iodine and extraction of radioactive methyl iodine are carried out, and the radioactive methyl iodine synthesis flask 101 provides the reaction space required to substitute methyl iodine and radioactive $Na^{131}I$.

The pressure reducing valve 102 plays a role in reducing the inner pressure of the device to induce the evaporation of organic solvent namely methyl iodine ($CH_3^{127}I$) so that the organic solvent is fractionated from aqueous $Na^{131}I$, and the methyl iodine-vapor fractionation unit 103 functions as a guide tube that enables the gasified $CH_3(^{127}I+^{131}I)$ to move upwards and the vapor having a boiling point of 100° C. to move downwards, thus increasing the separation of methyl iodine and vapor. Thereby, the present invention obviates the need for an additional humidifying agent ($H_2O+CaCl_2$) for removing aqua.

The methyl iodine-vapor condensate separator 104 collects methyl iodine. If aqua is present, methyl iodine having high specific gravity remains behind due to a difference in the specific gravity of the two solutions, whereas water having low specific gravity overflows, thus obtaining pure methyl iodine.

The gaseous methyl iodine condenser-methyl iodine condensate collector 105 condenses the gaseous methyl iodine in the upper recessed portion thereof using cold water or ice in order to aid the condensation of methyl iodine having a boiling point of about 42° C. Furthermore, the uncinate glass tube provided to the lower portion thereof enables the condensed methyl iodine to flow down along the wall of the device.

A better understanding of the present invention may be obtained via the following example which is set forth to illustrate, but is not to be construed as limiting the present invention.

Example 1

A $Na^{131}I$ solution and an organic solvent $CH_3^{17}I$ solution, which do not mix with each other, were mixed using a radioactive methyl iodine synthesis flask 101 of the device of FIG. 2, and the $CH_3I$ sample was diluted 10,000 times (10 µl was absorbed by 100 ml of impregnated activated carbon) at different times ranging from 0.1 hours to 16 hours and then the nuclear species thereof were analyzed using an HPGe gamma spectroscopy system (Gennie 2000, Canberra, USA) for 200 sec, thus obtaining specific radioactivity values of $^{131}$I (Table 2).

Figure 6:
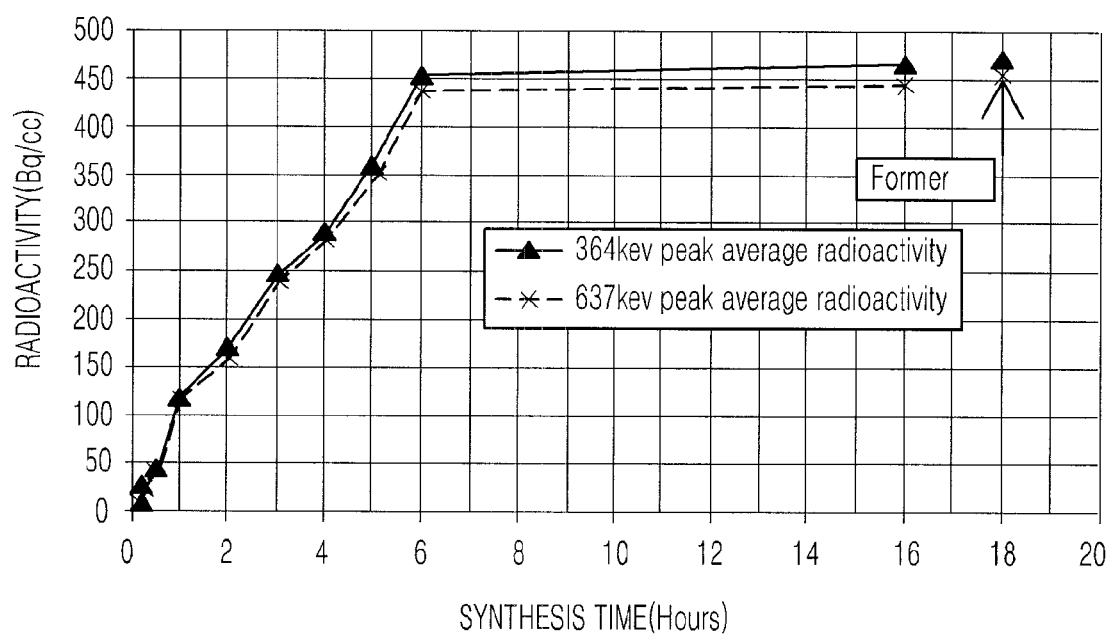
FIG. 6 shows a graph of changes in specific radioactivity of radioactive methyl iodine ($CH_3^{131}I$) prepared according to the present invention.

As such, in order to analyze nuclear species, the specific radioactivity values of $^{131}$I were measured two times and then averaged. Furthermore, changes in the specific radioactivity of 0.3645 MeV which is the major gamma energy peak and 0.6370 MeV which is the minor gamma energy peak are shown in FIG. 6.

In the method according to the present invention, the activated I. radical reaction occurred due to the beta and gamma energy ($\beta_{max}$=0.606 MeV (P=89%), $\gamma$=0.364 MeV (P=81%)) of $^{131}$I at the boundary of the two solutions resulting from mixing the radioactive isotope Na$^{131}$I aqueous solution and the volatile organic solvent CH$_3$$^{127}$I.

Figure 5:
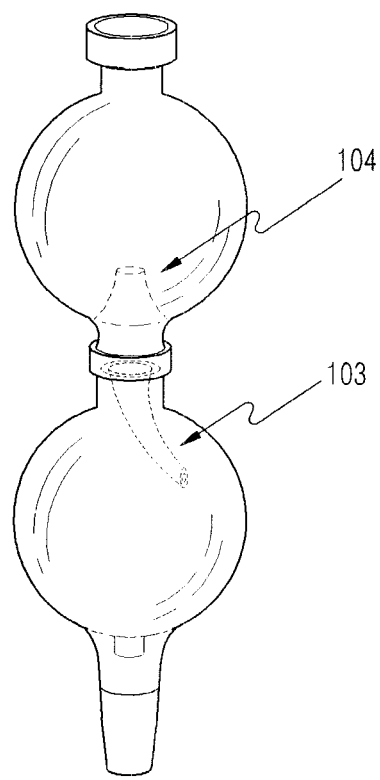
FIG. 5 shows the methyl iodine-vapor fractionation unit and the condensate separator of the device for synthesizing radioactive methyl iodine ($CH_3^{131}I$) according to the present invention.

Hence, 2I.→I$_2$ was not produced in the reaction of CH$_3$$^{127}$I+Na$^{131}$I+H$_2$O, whereas the production of I$_2$ could be seen upon reaction with Na$^{131}$I. Because the radioactive substitution is not the volume reaction but is the area reaction, specific radioactivity increased as a primary function over time for 6 hours as shown in FIG. 5. When 16 hours elapsed after 6 hours, specific radioactivity increased by about 3% (453.5→465.8 Bq/ml). Thus, when conducted for 6 hours the reaction is considered to be close to equilibrium.

The evaporation process resulted in 472.2 Bq/ml similar to when using a direct synthesis process. The intensities of radioactivity of the tracers obtained using two synthesis processes satisfied requirements ($10^3$-$10^5$ cpm) of ASTM D 3803 (actual value was $2.5\times10^4$ cpm).

The actual test time and whether there is leakage of the volatile material during the test are regarded as important in terms of radiation defense. The conventional evaporation synthesis process should handle 5 mCi RI (radioactive isotope) for 100 min or longer, whereas the direct synthesis process according to the present invention requires about 10 min to mix and separate, ultimately reducing the test time to 1/10 times, and also, the direct synthesis process obviates the need for evaporation, thus minimizing the probability of leaking the tracer.

TABLE 2

Specific Radioactivity of CH$_3$$^{131}$I synthesized using Direct Synthesis according to the Present Invention

| Time (h) | I-131 Activity of Primary Light Peak (Bq/ml) | | | I-131 Activity of Secondary Light Peak (Bq/ml) | | |
|---|---|---|---|---|---|---|
| | $1^{st}$ | $2^{nd}$ | Average | $1^{st}$ | $2^{nd}$ | Average |
| 0.1 | 9.63 | 9.66 | 9.64 | 8.47 | 8.84 | 8.64 |
| 0.2 | 26.79 | 25.74 | 26.26 | 24.40 | 24.24 | 24.32 |
| 0.5 | 44.22 | 39.92 | 42.07 | 42.82 | 38.48 | 40.65 |
| 1 | 119.4 | 113.2 | 116.3 | 116.9 | 110.0 | 113.5 |
| 2 | 167.9 | 169.2 | 168.5 | 156.9 | 160.4 | 158.7 |
| 4 | 287.8 | 293.8 | 290.8 | 277.3 | 284.5 | 280.9 |
| 6 | 450.2 | 456.7 | 453.5 | 437.8 | 437.8 | 437.8 |
| 16 | 453.4 | 478.0 | 465.7 | 429.5 | 460.4 | 445.0 |
| Former | 467.9 | 476.4 | 472.2 | 459.0 | 450.3 | 454.7 |

As described hereinbefore, the present invention provides a method and device for synthesizing a radioactive methyl iodine tracer. According to the present invention, radioactive sodium iodide (Na$^{131}$I) and methyl iodine (CH$_3$I) can be mixed at room temperature under reduced pressure, thus directly synthesizing the tracer, thereby shortening excessive synthesis time and decreasing the probability of radiation exposure due to leakage of volatile material during distillation.

Although the embodiments of the present invention have been disclosed for illustrative purposes, those skilled in the art will appreciate that a variety of different modifications, additions and substitutions are possible, without departing from the scope and spirit of the invention as disclosed in the accompanying claims. Accordingly, such modifications, additions and substitutions should also be understood as falling within the scope of the present invention.

What is claimed is:

1. A device for preparing a radioactive methyl iodide (CH$_3$$^{131}$I) tracer, the device comprising:
    a radioactive methyl iodide synthesis flask used for a substitution reaction between methyl iodide and radioactive iodine;
    a pressure reducing valve disposed in a side of the radioactive methyl iodide synthesis flask and used for reducing an inner pressure of the device;
    a methyl iodide-vapor fractionation unit positioned vertically above the radioactive methyl iodide synthesis flask, coupled directly to an upper portion of the radioactive methyl iodide synthesis flask, and separating methyl iodide from vapor, the methyl iodide-vapor fractionation unit having a bulb shape and including a guide tube inside an upper portion thereof so that gasified CH$_3$($^{127}$I+$^{131}$I) is moved upwards and vapor is moved downwards, thereby increasing separation of methyl iodide and vapor;
    a methyl iodide-vapor condensate separator positioned vertically above the methyl iodide-vapor fractionation unit, coupled directly to the upper portion of the methyl iodide-vapor fractionation unit, and collecting pure methyl iodide using a difference in specific gravity; and
    a gaseous methyl iodide condenser-methyl iodide condensate collector positioned vertically above the methyl iodide-vapor condensate separator, coupled directly to an upper portion of the methyl iodide-vapor condensate separator, condensing methyl iodide, and collecting condensed methyl iodide.

2. The device of claim 1, wherein the pressure reducing valve is used to reduce the inner pressure of the device in order to induce evaporation of an organic solvent CH$_3$$^{127}$I so that the organic solvent is fractionated from aqueous Na$^{131}$I.

3. The device of claim 1, wherein the methyl iodide-vapor condensate separator has a bulb shape and includes a conical protrusion inside a lower portion thereof so that methyl iodide having high specific gravity remains behind due to a difference in specific gravity, thereby collecting the pure methyl iodide.

4. The device of claim 1, wherein the gaseous methyl iodide condenser-methyl iodide condensate collector has a hemispheric shape and comprises
    a condenser having an upper recessed portion and aiding condensation of methyl iodide; and
    a collector including an uncinate glass tube at a lower portion thereof and collecting the condensed methyl iodide.

5. The device of claim 4, wherein the condenser condenses the gaseous methyl iodide in the upper recessed portion thereof using cold water or ice.

6. The device of claim 4, wherein the condensed methyl iodide flows down along a wall of the device through the uncinate glass tube.

7. A device for preparing a radioactive methyl iodide (CH$_3$$^{131}$I) tracer, the device comprising:
    a radioactive methyl iodide synthesis flask used for a substitution reaction between methyl iodide and radioactive iodine;

a pressure reducing valve disposed in a side of the radioactive methyl iodide synthesis flask and used to reduce an inner pressure of the device in order to induce evaporation of an organic solvent $CH_3{}^{127}I$ so that the organic solvent is fractionated from aqueous $Na^{131}I$;

a methyl iodide-vapor fractionation unit positioned vertically above the radioactive methyl iodide synthesis flask and coupled directly to an upper portion of the radioactive methyl iodide synthesis flask, the methyl iodide-vapor fractionation unit having a bulb shape and including a guide tube inside an upper portion thereof so that gasified $CH_3({}^{127}I+{}^{131}I)$ is moved upwards and vapor is moved downwards thereby increasing separation of methyl iodide from vapor;

a methyl iodide-vapor condensate separator positioned vertically above the methyl iodide-vapor fractionation unit and coupled directly to the upper portion of the methyl iodide-vapor fractionation unit, the methyl iodide-vapor condensate separator having a bulb shape and including a conical protrusion inside a lower portion thereof so that methyl iodide having high specific gravity remains behind due to a difference in specific gravity, thereby collecting pure methyl iodide; and a gaseous methyl iodide condenser-methyl iodide condensate collector positioned vertically above the methyl iodide-vapor condensate separator and coupled directly to an upper portion of the methyl iodide-vapor condensate separator, the gaseous methyl iodide condenser-methyl iodide condensate collector having a hemispheric shape and comprising a condenser having an upper recessed portion and aiding condensation of methyl iodide; and a collector including an uncinate glass tube at a lower portion thereof and collecting condensed methyl iodide.

8. The device of claim 7, wherein the condenser condenses the gaseous methyl iodide in the upper recessed portion thereof using cold water or ice.

9. The device of claim 7, wherein the condensed methyl iodide flows down along a wall of the device through the uncinate glass tube.

* * * * *